(12) United States Patent
Birsner et al.

(10) Patent No.: US 11,634,487 B2
(45) Date of Patent: *Apr. 25, 2023

(54) DIAGNOSTIC METHOD

(71) Applicant: AVA Lifescience GmbH, Denzlingen (DE)

(72) Inventors: Ulrich Birsner, Freiburg im Breisgau (DE); Hassan Jumaa, Blaubeuren (DE); Holger Klapproth, Freiburg im Breisgau (DE); Marc A. Kessemeier, Emmendingen (DE)

( * ) Notice: Subject to any disclaimer, the term of this patent is extended or adjusted under 35 U.S.C. 154(b) by 271 days.

This patent is subject to a terminal disclaimer.

(21) Appl. No.: 16/625,754

(22) PCT Filed: Jul. 5, 2018

(86) PCT No.: PCT/EP2018/068316
§ 371 (c)(1),
(2) Date: Feb. 11, 2020

(87) PCT Pub. No.: WO2019/008128
PCT Pub. Date: Jan. 10, 2019

(65) Prior Publication Data
US 2020/0209246 A1    Jul. 2, 2020

(30) Foreign Application Priority Data

Jul. 7, 2017  (EP) .................................. 17001166
Jul. 7, 2017  (EP) .................................. 17001167
Mar. 19, 2018  (EP) .................................. 18162666

(51) Int. Cl.
*C07K 16/28*  (2006.01)
*A61P 35/02*  (2006.01)
*C07K 16/30*  (2006.01)
*G01N 33/574*  (2006.01)

(52) U.S. Cl.
CPC .......... *C07K 16/2803* (2013.01); *A61P 35/02* (2018.01); *C07K 16/3061* (2013.01); *G01N 33/57492* (2013.01); *C07K 2317/34* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 10,035,853 B2 * | 7/2018 | Arathoon ........... | A61K 47/6849 |
| 2004/0197328 A1 | 10/2004 | Young | |
| 2015/0018531 A1 | 1/2015 | Saunders | |
| 2020/0199225 A1 * | 6/2020 | Birsner .............. | C07K 16/2803 |

FOREIGN PATENT DOCUMENTS

WO    2014179714 A1    11/2014

OTHER PUBLICATIONS

Duhren-von Minden et al, Nature (2012) 489:309-312. (Year: 2012).*
Hacken et al, Biochimica et Biophysica Acta 1863 (2016) 401-413 (Year: 2016).*
Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Claudia Minici et al. "Distinct homotypic B-cell receptor interactions shape the outcome of chronic lymphocytic leukaemia," Nature Communications, vol. 8, Jun. 9, 2017 (Jun. 9, 2017), p. 15746, DOI: 10.1038/ncomms15746, XP055481551.
Marcus Duhren-Von Minden et al. "Chronic lymphocytic leukaemia is driven by 1-17 antigen-independent cell-autonomous signalling," Nature, GB, vol. 489, No. 7415, Aug. 12, 2012 (Aug. 12, 2012), pp. 309-312, DOI: 10.1038/nature11309, ISSN: 0028-0836, XP055481577.
Jose L. Sanchez-Trincado et al. "Fundamentals and Methods for T- and B-Cell Epitope Prediction," Journal of Immunology Research, vol. 2017, Dec. 28, 2017 (Dec. 28, 2017), pp. 1-14, DOI: 10.1155/2017/2680160, ISSN: 2314-8861, XP055469700.
Bojarczuk Kamil et al. "B-cell receptor signaling in the pathogenesis of lymphoid malignancies," Blood Cells, Molecules and Diseases, Lajolla, US, vol. 55, No. 3, Jul. 11, 2015 (Jul. 11, 2015), pp. 255-265, DOI: 10.1016/J.BCMD.2015.06.016, ISSN: 1079-9796, XP029252301.
International Search Report, PCT/EP2018/068316, dated Sep. 3, 2018, EPO, Rijswik, Netherlands.

(Continued)

*Primary Examiner* — Julie Wu
*Assistant Examiner* — Cheom-Gil Cheong
(74) *Attorney, Agent, or Firm* — Saffire IP; Daren P. Nicholson

(57) ABSTRACT

The present invention relates to the field of production, identification and selection of biological binding molecules such as antibodies or fragments thereof, as well as to diagnostic procedures using them in the diagnosis of cancers, in particular malignant B-cell neoplasia. The binding molecules are able to selectively bind to autonomously active or autonomously activated B-cell receptors, the autonomously active or autonomously activated B-cell receptors being characterized by the presence of structural domains to which the binding molecule selectively binds and which are responsible for the autonomously active or autonomously activated state of the B-cell receptors.

8 Claims, 2 Drawing Sheets
Specification includes a Sequence Listing.

(56) References Cited

OTHER PUBLICATIONS

English translation, International Search Report, PCT/EP2018/068316, dated Sep. 3, 2018, EPO, Rijswik, Netherlands.
Almagro & Fransson, Frontiers in Bioscience 2008; 13:1619-33 (Year: 2008).
Gura (Science, 1997, 278: 1041-1042) (Year: 1997).
Kaiser (Science, 2006, 313: 1370) (Year: 2006).
Jena et al. (Blood Aug. 19, 2010 116(7): 1035-1044) (Year: 2010).
Janeway CA Jr, Travers P, Walport M, et al. (Immunobiology: The Immune System in Health and Disease. 5th edition. New York: Garland Science; 2001. Appendix I. Immunologists' Toolbox. Available from: https://www.ncbi.nlm.nih.gov/books/N BK10755/) (Year: 2001).
Chames et al. (British J. of Pharmacology, 2009, 157, 220-233) (Year: 2009).

* cited by examiner

SEQUENCE LISTING

<160> NUMBER OF SEQ ID NOS: 17

<210> SEQ ID NO 1
<211> LENGTH: 10
<212> TYPE: PRT
<213> ORGANISM: Homo sapiens
<220> FEATURE:
<223> OTHER INFORMATION: Autonomously active region Subset 2/1

<400> SEQUENCE: 1

Lys Leu Thr Val Leu Arg Gln Pro Lys Ala
1               5                   10

<210> SEQ ID NO 2
<211> LENGTH: 8
<212> TYPE: PRT
<213> ORGANISM: Homo sapiens
<220> FEATURE:
<223> OTHER INFORMATION: Autonomously active region Subset 2/2

<400> SEQUENCE: 2

Val Ala Pro Gly Lys Thr Ala Arg
1               5

<210> SEQ ID NO 3
<211> LENGTH: 10
<212> TYPE: PRT
<213> ORGANISM: Homo sapiens
<220> FEATURE:
<223> OTHER INFORMATION: Autonomously active region Subset 4/1

<400> SEQUENCE: 3

Pro Thr Ile Arg Arg Tyr Tyr Tyr Tyr Gly
1               5                   10

<210> SEQ ID NO 4
<211> LENGTH: 9
<212> TYPE: PRT
<213> ORGANISM: Homo sapiens
<220> FEATURE:
<223> OTHER INFORMATION: Autonomously active region Subset 4/2

<400> SEQUENCE: 4

Asn His Lys Pro Ser Asn Thr Lys Val
1               5

<210> SEQ ID NO 5
<211> LENGTH: 116
<212> TYPE: PRT
<213> ORGANISM: Homo sapiens
<220> FEATURE:
<223> OTHER INFORMATION: Autonomously active region Subset 2 VH

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Leu Tyr Tyr Cys
                85                  90                  95

Ala Arg Asp Gln Asn Ala Met Asp Val Trp Gly Gln Gly Thr Thr Val
            100                 105                 110

Thr Val Ser Ser
        115

<210> SEQ ID NO 6
<211> LENGTH: 215
<212> TYPE: PRT
<213> ORGANISM: Homo sapiens
<220> FEATURE:
<223> OTHER INFORMATION: Autonomously active region Subset 2 LC

<400> SEQUENCE: 6

Ser Tyr Glu Leu Thr Gln Pro Pro Ser Val Ser Val Ala Pro Gly Lys
1               5                   10                  15

Thr Ala Arg Ile Thr Cys Ala Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Gly Ser Asp His
                85                  90                  95

Pro Trp Val Phe Gly Gly Gly Thr Lys Leu Thr Val Leu Arg Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 7
<211> LENGTH: 224
<212> TYPE: PRT
<213> ORGANISM: Homo sapiens
<220> FEATURE:
<223> OTHER INFORMATION: Autonomously active region Subset 4 HC

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Ser Pro Gly Lys Gly Leu Glu Trp Ile
        35                  40                  45
```

Gly Glu Ile Asn His Ser Gly Ser Thr Thr Tyr Asn Pro Ser Leu Lys
                50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                    85                  90                  95

Arg Gly Tyr Gly Asp Thr Pro Thr Ile Arg Arg Tyr Tyr Tyr Tyr Gly
               100                 105                 110

Met Asp Val Trp Gly Gln Gly Thr Thr Val Thr Val Ser Ser Ala Ser
               115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Cys Leu Gln Ser Ser Gly Leu Tyr Ser Leu Ser
                180                 185                 190

Ser Val Val Thr Val Pro Ser Ser Leu Gly Thr Gln Thr Tyr Ile
                195                 200                 205

Cys Asn Val Asn His Lys Pro Ser Asn Thr Lys Val Asp Lys Lys Cys
210                 215                 220

<210> SEQ ID NO 8
<211> LENGTH: 220
<212> TYPE: PRT
<213> ORGANISM: Homo sapiens
<220> FEATURE:
<223> OTHER INFORMATION: Autonomously active region Subset 4 LC

<400> SEQUENCE: 8

Asp Ile Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asp Arg Asp Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Leu Tyr Tyr Cys Met Gln Gly
                85                  90                  95

Thr His Trp Pro Pro Tyr Thr Phe Gly Gln Gly Thr Lys Val Glu Ile
               100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

-continued

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 9
<211> LENGTH: 119
<212> TYPE: PRT
<213> ORGANISM: Mus musculus
<220> FEATURE:
<223> OTHER INFORMATION: AVA mAb01 HC

<400> SEQUENCE: 9

Gln Val Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Arg Gly Gly Thr Asp Ser Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Ser Arg Tyr Asp Glu Glu Glu Ser Met Asn Tyr Trp Gly Gln Gly
            100                 105                 110

Thr Ser Val Thr Val Ser Ser
        115

<210> SEQ ID NO 10
<211> LENGTH: 107
<212> TYPE: PRT
<213> ORGANISM: Mus musculus
<220> FEATURE:
<223> OTHER INFORMATION: AVA mAb01 LC

<400> SEQUENCE: 10

Gln Ile Val Leu Thr Gln Ser Pro Ala Ser Leu Ser Ala Ser Val Gly
1               5                   10                  15

Glu Thr Val Thr Ile Thr Cys Arg Ala Ser Gly Asn Ile His Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Asn Thr Pro Pro
                85                  90                  95

Thr Phe Gly Ala Gly Thr Lys Leu Glu Leu Lys
            100                 105

<210> SEQ ID NO 11
<211> LENGTH: 8
<212> TYPE: PRT
<213> ORGANISM: Mus musculus
<220> FEATURE:
<223> OTHER INFORMATION: AVA mAb01 CDR1 HC

```
<400> SEQUENCE: 11

Gly Phe Ser Leu Thr Ser Tyr Gly
1               5

<210> SEQ ID NO 12
<211> LENGTH: 7
<212> TYPE: PRT
<213> ORGANISM: Mus musculus
<220> FEATURE:
<223> OTHER INFORMATION: AVA mAb01 CDR2 HC

<400> SEQUENCE: 12

Ile Trp Arg Gly Gly Gly Thr
1               5

<210> SEQ ID NO 13
<211> LENGTH: 13
<212> TYPE: PRT
<213> ORGANISM: Mus musculus
<220> FEATURE:
<223> OTHER INFORMATION: AVA mAb01 CDR3 HC

<400> SEQUENCE: 13

Ala Arg Ser Arg Tyr Asp Glu Glu Glu Ser Met Asn Tyr
1               5                   10

<210> SEQ ID NO 14
<211> LENGTH: 6
<212> TYPE: PRT
<213> ORGANISM: Mus musculus
<220> FEATURE:
<223> OTHER INFORMATION: AVA mAb01 CDR1 LC

<400> SEQUENCE: 14

Gly Asn Ile His Ser Tyr
1               5

<210> SEQ ID NO 15
<211> LENGTH: 4
<212> TYPE: PRT
<213> ORGANISM: Mus musculus
<220> FEATURE:
<223> OTHER INFORMATION: AVA mAb01 CDR2 LC

<400> SEQUENCE: 15

Asn Ala Lys Thr
1

<210> SEQ ID NO 16
<211> LENGTH: 9
<212> TYPE: PRT
<213> ORGANISM: Mus musculus
<220> FEATURE:
<223> OTHER INFORMATION: AVA mAb01 CDR3 LC

<400> SEQUENCE: 16

Gln His Phe Trp Asn Thr Pro Pro Thr
1               5

<210> SEQ ID NO 17
<211> LENGTH: 8
<212> TYPE: PRT
<213> ORGANISM: Mus musculus
<220> FEATURE:
<223> OTHER INFORMATION: Autonomously active region Subset 4/2
```

```
<400> SEQUENCE: 17

Val Ser Ser Ala Ser Thr Lys Gly
1               5
```

DIAGNOSTIC METHOD

The instant application contains a Sequence Listing, which has been submitted electronically in ASCII format and is hereby incorporated by reference in its entirety. Said ASCII copy, created on Mar. 3, 2020, is named 32101-301101 Substitute Sequence Listing and is 11,148 bytes in size.

FIELD OF INVENTION

The present invention relates to the field of the production, identification and selection of antibodies or fragments thereof and to their use in the diagnosis of cancers, such as, in particular, malignant B-cell neoplasia.

BACKGROUND OF THE INVENTION

Malignant B-cell neoplasias are generally meant to denote malignant diseases of the hematopoietic or lymphatic system. They include clinical pictures such as e.g. leukaemia and in a broader sense belong to cancer diseases. Leukaemias are characterized by a greatly increased formation of dysfunctional white blood cell precursors, also known as leukaemia cells. These cells spread in the bone marrow, displace the usual blood formation there and usually accumulate strongly in the peripheral blood. They can infiltrate the liver, spleen, lymph nodes and other organs and thereby impair their function. The disturbance in blood formation leads to a reduction in normal blood components, which can lead to anemia due to a lack of oxygen-transporting red blood cells, a lack of hemostatic platelets, and a lack of mature functional white blood cells.

Depending on the course of the disease, a distinction is made between acute and chronic leukaemia. Acute leukaemias are life-threatening diseases which, if left untreated, lead to death within a few weeks or months. Chronic leukaemias, on the other hand, usually run for several years and are often low in symptoms in their early stages.

The most important forms of leukaemia are:
acute myeloid leukemia (AML)
chronic myeloid leukemia (CML)
acute lymphatic leukemia (ALL)
chronic lymphatic leukemia (CLL).

Leukaemias are usually treated with chemotherapy. More recent therapies are increasingly using monoclonal antibodies such as e.g. GA101 (Obinutuzumab), which acts as a CD20 antibody similar to Rituximab and Ofatumumab and is used to treat chronic lymphatic leukemia (CLL). By using these antibodies, the remission-free time can be extended by approx. 10 months.

Other malignant diseases of the hematopoietic or lymphatic system (malignant B-cell neoplasia) affect lymphomas, such as e.g. Hodgkin lymphoma and the B-cell variants of non-Hodgkin lymphomas.

If antibodies against receptors are generated, animals are usually immunized with the receptor (purified, cloned, or as peptide fragments) and hybridoma cells are generated. These hybridoma cells produce antibodies which are then tested in cell systems using ELISA or expressed receptors. Conventionally, established cell lines are used for this because only these can be cultivated easily. Antibodies can be generated which bind relatively specifically to a certain receptor type (e.g. Anti-IgG1, Anti-IgE). However, this often leads to cross-reactions with other receptors or other epitopes.

For a diagnostic application of BCR antibodies, it is usually not sufficient to use only one antibody against the BCR in general, as such a broad-spectrum use can lead to false positive results. Rather, it would be desirable to provide an antibody that selectively binds to a receptor that exhibits a (pathophysiological) activation, in particular autonomic activation. Such an antibody is not known in the state of the art and a process for its production or extraction by selection does not exist.

State-of-the-art therapies for the treatment of leukaemias are very stressful for the patient. In general it can be summarized that the undesired side effects of the therapy and the often insufficient effect of the drugs lead to a high death rate of this disease, because not only tumor cells, but also healthy cells of the immune system are damaged. In addition, there is often no cure, but only the creation of a certain period of time in which the disease is demission-free. Therefore, it is important for the identification and selection of patients to be treated and for the development of an individual therapy plan to have diagnostic tools and diagnostic procedures available using them to differentially detect certain forms of malignant B-cell neoplasia.

DETAILED DESCRIPTION OF THE INVENTION

Figure 1:
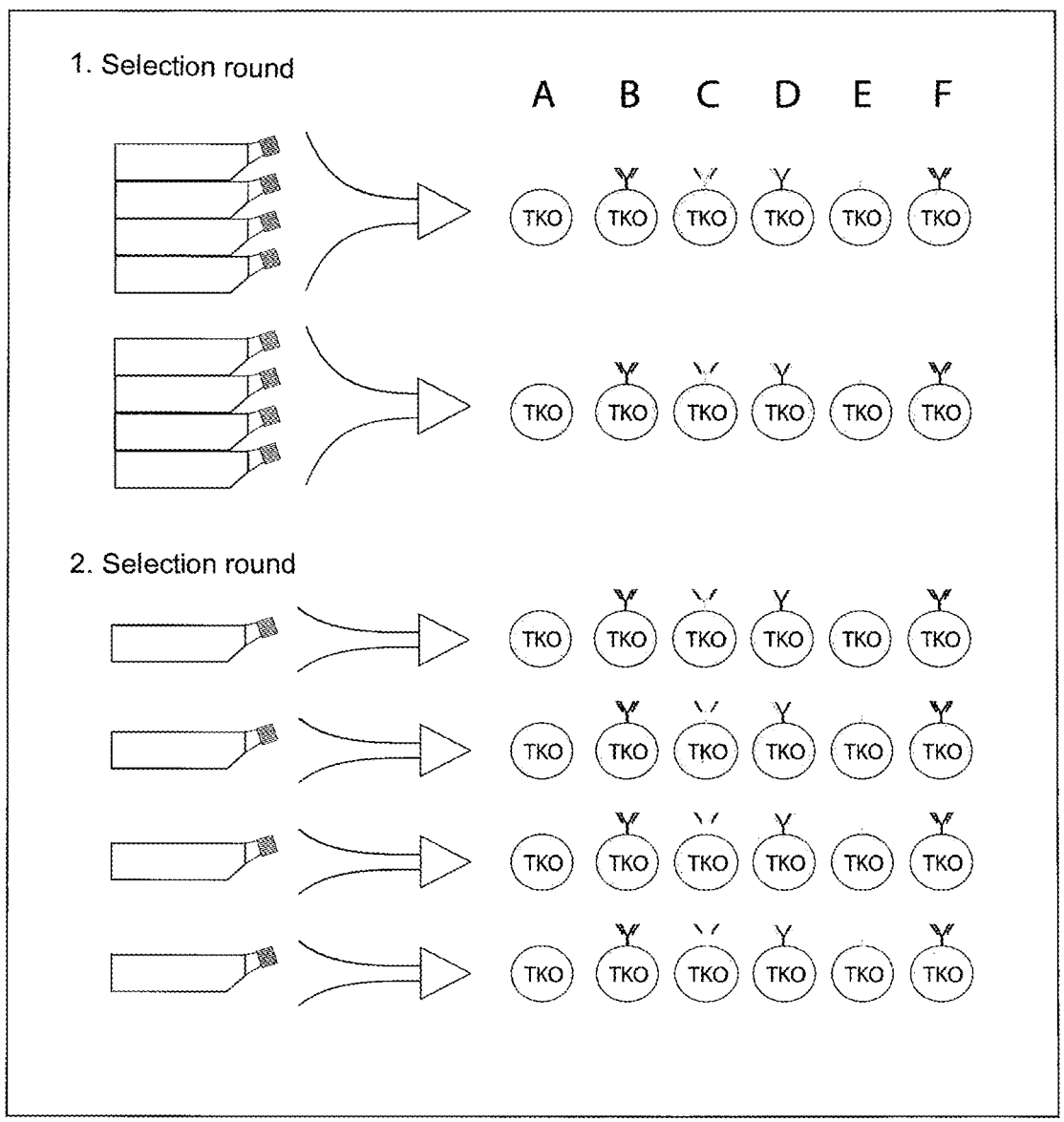
FIG. 1 illustrates an exemplary selection matrix for the selection of a CLL subset 2 BCR used for identification and selection of positive binding clones from among TKO cells expressing different versions of a "BCR of Interest."

The task of the present invention is therefore to provide alternative concepts and means, such as, in particular, alternative antibodies for diagnostic use, to overcome the existing problems of the state of the art.

Before the individual aspects of the present invention are discussed in detail, relevant terms used in the present description are clarified.

The term "neoplasia" used herein generally refers to the formation of new body tissue. If this is a pathological or malignant manifestation, one speaks of a malignant neoplasia. Malignant B-cell neoplasia is therefore a malignant and uncontrolled formation of new tissue by B-cells, whereby this term applies equally to all B-cell associated cancers such as leukaemias and B-cell lymphomas.

The term "biological binding molecules" is used herein to refer, for example, but not exclusively, to antibodies including fusion proteins. Advantageously, and therefore preferably, such an antibody is selected from the group consisting of an IgG antibody, an IgM antibody, a humanized IgG antibody, and a human antibody into which the recognition sequence of the epitope is inserted. Such a binding molecule may also be provided in the form of a functional fragment of the whole antibody, e.g. as a Fab fragment. A binding molecule may also include other areas or additional entities, the use of which is advantageous in diagnostic applications. These can be fluorescent dyes (e.g.: FITC, R-Phycoerythrin (R-PE), Allophycocyanin (APC)) or biotin as well as other substances known to the expert using flow cytometry. In addition, a binding molecule can also be used together with substrate converting enzymes (e.g. HRP) in immunohistochemical processes. Furthermore, fusion proteins can also be provided for diagnostic purposes, in which fluorescent proteins such as the green fluorescent protein (GFP) are coupled to the FC part of the antibody for detection.

The function of the B-cell receptor or B-cell receptor complex (BCR) on the surface of a B-cell is to recognize and bind to pathogens, which is why it can be regarded as a membrane-bound antibody. This binding leads to a conformational change in the BCR, triggering a signaling cascade that ultimately leads to an activation of the B cell. The BCR is formed in great diversity in maturing B cells.

The development of B-cells takes place in humans and also in some other mammals in the bone marrow or in the fetal liver. The signals necessary for the development programme are received by the developing lymphocytes from so-called stromal cells. In B-cell development, the formation of a functioning B-cell receptor (the membrane-bound form of the 'antibody') is of crucial importance. Only with this antigen receptor are mature B cells later able to recognize foreign antigens and bind them to hostile structures by forming corresponding antibodies. The antigen specificity of the receptor is determined by linking certain gene segments. The segments are called V, D and J segments, which is why the process is called V(D)J recombination. These segments, which form the antigen-binding part of the B-cell receptor, are rearranged. The entire receptor consists of two identical light protein chains and two identical heavy protein chains, the heavy and light chains respectively being linked by disulphide bridges. In VDJ recombination, the V, D and J segments of the heavy chain of the B-cell receptor are linked first, followed by the V and J segments of the light chain. Only if the genes are successfully rearranged, which is referred to as productive gene rearrangement, can the cell move on to the next developmental step.

B cells, which react to the body's own antigens during their maturation in the bone marrow, die in the vast majority of cases by apoptosis. In the blood of healthy people small amounts of autoreactive cells can be detected, among others against thyroglobulin or collagen (Abul K. Abbas: *Diseases of Immunity* in Vinay Kumar, Abul K. Abbas, Nelson Fausto: *Robbins and Cotran—Pathologic Basis of Disease;* 7th edition; Philadelphia 2005, p. 224f).

Since the process of generating such a BCR is based on a random aggregation of gene segments, it can happen that the newly formed BCR undesirably recognizes endogenous structures and is thus "permanently activated". In order to prevent the formation of such a "permanently active or activated" BCR, various protective mechanisms exist in the body. However, if these are overcome due to a pathological change in the developing B cell, a malignant or autoimmune disease can develop.

In contrast, an "autonomously active" or "autonomously activated" BCR is a special type of a permanently active BCR. While the conventional activation is based on an external antigen (see above), the autonomously active BCR results from its interaction with membrane structures on the surface of the same cell. For the clinical picture of CLL, an autonomic activation-triggering interaction between BCRs adjacent to each other on the surface of the same cell could be shown (M. Dühren-von Minden et. al; Nature 2012). Another example of an autonomously active BCR is the pre-BCR, which is expressed as a development check during the development of a B cell. In addition to the interaction of neighboring receptors (BCR:BCR), an interaction between receptor and a membrane protein (BCR:membrane protein) can also lead to an autonomously active or activated BCR.

The solution to these problems according to the invention is based on the surprising realization that tumor cells of patients with CLL display B-cell receptors which are autonomously active or autonomously activated, and that these autonomously active or activated receptors are characterized by the presence of common epitopes that cannot be detected in corresponding receptors of healthy cells of the same patient. These cells can thus be specifically recognized and, if necessary, treated by an antibody due to the presence of autonomously active B-cell receptors, which are characterized by the presence of the above-mentioned epitopes, so that healthy B-cells without this characteristic are not affected, so that the treatment can be carried out much more specifically and with fewer undesired side effects.

In the course of the numerous experiments carried out for this invention, however, it turned out surprisingly that antibodies with special specificity for these modified receptor regions (epitopes) cannot be produced and selected using conventional standard methods. Only after the experimental conditions had been adapted in such a way that genetically modified cells whose modified B-cell receptors were in a native and activated state could suitable antibodies with the desired and required specificity be obtained within the framework of binding studies. In other words, it is essential for the solutions proposed according to the invention that the cells used in binding studies to select suitable diagnostic antibodies present their modified regions (epitopes) in a largely native and activated form. This showed that so-called pro-/pre-B cells are particularly suitable due to their physiological constitution. The provision of such specific antibodies and functional fragments of the same, which also possess this specific binding behavior, thus allows a tumor-specific diagnosis and, if necessary, a subsequent therapy, which is characterized by a significantly improved treatment success and, thanks to the reduction of undesired systemic effects, a significantly increased therapy success.

As already mentioned, this invention provides diagnostic procedures using biological binding molecules in the form of antibodies or functional fragments thereof and a process for the production (identification and selection) of such binding molecules which selectively bind to the modified epitopes of autonomously active membrane-bound immunoglobulins of B-cell neoplasia. According to a preferred embodiment of the invention, the biological binding proteins selectively bind to those autonomously active B-cell receptors on B-cells that occur in immunological (e.g. autoimmune) diseases and are causally related to these (e.g. allergies, ulcerative colitis, diabetes mellitus type 1, multiple sclerosis, psoriasis, rheumatic fever, rheumatoid arthritis, celiac disease).

Membrane-bound immunoglobulins are well-suited targets for a targeted, i.e. specific immunotherapy. During B-cell development in the bone marrow, each individual B-cell precursor generates its own and almost unique B-cell receptor (BCR) by rearranging individual gene segments.

Two variants (Subset 2; Subset 4) of the autonomously active BCR are known, which differ from each other with regard to their respective characterizing molecular motif (epitopes) (Minici, C. et al., Distinct homotypic B-cell receptor interactions shape the outcome of chronic lymphocytic leukaemia, Nature Comm. (2017)). However, the expert is aware that, in addition to CLL subset 2 and subset 4 BCRs, there are other BCRs with the property of an autonomous activity. Both variants have different short amino acid sequences that are specific for these variants. The expert knows that other CLL-B cell receptors are autonomously active in addition to the subsets listed. The region of subset 2 relevant for the autonomously active functionality of the receptor is characterized by the amino acid sequences KLTVLRQPKA (SEQ ID NO. 1) and VAPGKTAR (SEQ ID NO. 2) of the light chain, while the region of subset 4 relevant for the autonomously active functionality of the receptor is defined by the amino acid sequences PTIRRYYYYG (SEQ ID NO. 3) and NHKPSNTKV (SEQ ID NO. 4) of the variable part of the heavy chain. The sequences for subsets 2 and 4 used to generate murine antibodies during immunization are listed in SEQ ID NOS. 5 and 6 (vHC; LC) and 7 and 8 (vHC; LC), respectively. For the sake of completeness, SEQ ID NO. 17 (VSSASTKG) provides a further target sequence or epitope with specificity for the variable part of the heavy chain of a BCR of subset 4. In addition to the target sequences (epitopes) responsible for the formation of the autonomously active state of the BCR (subset 4) according to SEQ ID NOS. 3 and 4, the sequence according to SEQ ID NO. 17 thus represents a further characteristic property of this subset.

It should be noted that the finding and characterization of subsets 2 and 4 as two variants of the B cell receptor in patients with critical disease progression is based on the study of numerous individual case studies and therefore does not mean that in a possible large number of other subtypes of the BCR the same target sequences (epitopes) are not present for the two known subtypes and correlate with a severe disease progression.

Although antibodies against both of these subsets should in principle be generated by standard methods, e.g. in mice, it was surprisingly observed that immunization using peptides does not lead to the formation of the desired specific antibodies. Immunization using individual chains of the receptor, such as the use of the light chain of the BCR comprising the modified sequence regions, did not bring the desired success either, which is why mice were finally immunized with the recombinantly produced soluble form of the BCR (cf. SEQ ID NOS. 5 and 6). Immune cells with the desired specificity could then be obtained from these mice and transformed into hybridoma cells by cell fusion. Surprisingly, the active antibodies could not be identified by ELISA or other standard methods. However, the clones identified as potential binding partners in a first step by ELISA proved to be either non-specifically binding or not binding to the autonomously active receptor (including SEQ ID NOS. 1 and 2) after selection and therefore had to be discarded.

The methods used up to this point not only included standard methods such as ELISA and SPR, but also intracellular expression in fibroblasts with intracellular FACS staining as binding control.

After elaborate further test series it could be shown that a successful selection of suitable binding molecules according to the invention cannot be carried out with free receptors or their fragments nor with membrane-bound or intracellular receptor fragments. Instead, it was observed that selection was only possible using a cell system in which the complete and functional B-cell receptor was presented membrane-bound. It is of great importance that the BCR with its modified regions (epitopes) is autonomously active in or presented on these cells. Only with this approach, whose conditions reflect a largely physiological-native in situ scenario, was it possible to identify an antibody that binds highly specifically and selectively only to the tumor cells, i.e. to B cells that express a BCR with an epitope on their cell membrane that is characteristic for the subset-2 or subset-4 of this cell type, but not to other B cells or their receptors (BCRs), which by definition do not represent B cells of subset 2 or 4. In other words, the proposed binding molecule selectively binds to autonomously active or autonomously activated B-cell receptors characterized by the presence of structural domains or epitopes (target sequences) that are responsible for the autonomously active or activated state of the B-cell receptors. The selective binding behavior of the binding molecule proposed for diagnostic use according to the invention means that it does not bind to receptors or other membrane structures of B-cells that do not have a structural domain or epitope that is responsible for the autonomously active or activated state of the B-cells. Thus, the proposed binding molecule does not selectively bind to target sequences of the B cell receptor which are not characteristic for subset 2 or subset 4, and in particular does not bind to a B cell receptor which does not contain any of the sequences SEQ ID NOS. 1, 2, 3 and/or 4.

It has also been shown that the use of arrested pro-/pre-B cells obtained from Triple Knockout (TKO) mice, despite their difficult handling and elaborate extraction, is particularly well suited to express these receptors and be used in a test system to identify these receptors. The stage of pro-/pre-B cells is naturally designed to carry out the maturation and selection of BCRs, and the cells of this stage are particularly suitable for correctly folding even "difficult" BCR components due to their enzymatic properties (chaperones, etc.) and presenting them on their surface in a sufficiently physiologically native form. The deletions (knockouts) described below prevent the desired BCR from being altered by recombination or the use of the surrogate light chain. By using these cells or this cell type of arrested pro-/pre-B cells for the expression and presentation of BCRs in the context of a selection of antibodies with selective-specific binding behavior towards autonomously active or activated B cell receptors, a selection platform is provided which, in comparison with the systems conventionally used for selection in the state of the art, is characterized by a much higher quality which justifies the high expenditure of the use of primary TKO cells and their cultivation over a few passages, respectively.

After the selection of suitable hybridoma cells described above, the antibodies suitable for diagnostic purposes in the form of monoclonal antibodies could be obtained in larger quantities. The binding site of the antibody could be determined by sequencing the DNA of these cells (cf. SEQ ID NOS. 9 and 10). Such procedures are known to the expert and are also commercially available. It is advantageous to obtain a larger number of hybridoma cells and select those with the best binding activity (specificity and binding strength/affinity).

The resulting genetic information about the binding site was used to introduce the coding sequence into an expression plasmid in order to generate a monoclonal antibody with the desired specificity by the usual recombination route. Due to their unique specificity, these antibodies showed better diagnostic specificity compared to conventional diagnostic tools. The expert is aware that these recombinant antibodies can be produced in large quantities using biotechnological methods. For the purification of the synthesized antibodies standardized methods can be applied, e.g. combinations of precipitation, filtration and chromatography, which are sufficiently well known to the expert. It should be noted that the antibodies should not be denatured and possible foreign substances such as proteins, pyrogens and toxins should be removed quantitatively.

The desired antibodies are preferably expressed in systems in which the antibody undergoes glycosylation, in particular human glycosylation. Such systems are well known to experts and include the use of insect cells (S2 cells), mammalian cells (CHO cells) and, particularly preferred, human cells such as HEK293T cells.

The sufficiently purified antibody can in itself be therapeutically effective if it has an isotype that evokes a specific immune response, such as an IgG subtype that leads to an immune response against the tumor via Fc receptors.

The antibody may also be present as a fragment. As with a complete antibody, the fragment to be used is modified for diagnostic use by coupling to e.g. a fluorescent dye, biotin, and/or an enzymatic subunit in the usual way.

For diagnostic use, the antibody is preferably used in standardized procedures such as flow cytometry or immunohistochemistry. Preferably, the antibodies, biological binding molecules or functional fragments thereof proposed for diagnostic purposes have a murine backbone. Detection in the flow cytometer is preferably performed using secondary antibodies, or alternatively preferably using fluorescent dyes bound directly to the antibodies, biological binding molecules or functional fragments of the same.

For stable storage, it may be advantageous to provide the antibody or its fragments in a stabilized form, which is accordingly preferred. This can be done, for example, by drying with a stabilizing salt buffer. Such a buffer can be, for example, a phosphate-buffered saline solution (PBS), as the expert knows. A suitable form of drying is e.g. freeze drying or lyophilization.

Individual aspects of the present invention are explained in more detail below using examples.

Before detailed explanations of the experimental procedure are given, please refer to the following explanations.

The production and identification of antibodies that selectively bind to the modified B-cell receptors was characterized by major and unforeseen problems. The hybridomas were generated using standard methods. The supernatant from the hybridoma groups was pooled and examined for positive binding events by ELISA (soluble B-cell receptors on the ELISA plate). Positive pools were isolated and the individual clones were tested. Surprisingly, no more positive clones were identified in the ELISA. The positive ELISA signals of the pools subsequently turned out to be unspecific bonds.

In order to create better epitopes for the recognition of the antibodies, the light chain of the BCR was now expressed in fibroblasts. This should ensure the correct folding of the protein carrying the motif responsible for the autonomous signal (epitope). Intracellular FACS analyses were performed with these cells. No positive clone (antibody) could be identified.

For this reason, RAMOS cells (human Burkitt lymphoma cell line) were modified in another experiment so that they exhibited functional modified BCRs. This should ensure completely correct biosynthesis, folding and modification of the BCR. The cell's own BCR was deleted using CRISPR and then the "CLL receptor" was molecularly reconstituted (electroporation of CMV vectors). These cells were used to test positive binding events. Here, too, no positive clone was detectable with FACS.

Surprisingly, however, the use of murine TKO ('Triple Knockout') cells (arrested pro-/pre-B cells), into which the CLL receptor was introduced by means of a gene shuttle, produced a positive clone. And this despite the fact that the human cell system could not guarantee this. These cells have the following knockouts in their genome as a special feature:

the knockout of RAG2 prevents the somatic recombination of own heavy and light immunoglobulin chains, which is why the endogenous formation of a BCR is excluded. This leads to arrest, blocking or 'freezing' of correspondingly treated B cells at this stage of development. It is known that RAG1 and RAG2 form a complex which makes the usual VDJ rearrangement possible in the first place, which is why a knockout of RAG1 is a means with the same effect and thus an alternative to the knockout of RAG2 and is covered by the teaching according to the invention.

the deletion of Lambda5, a part of the surrogate Light Chain, prevents the formation of a pre-BCR. Since the pre-BCR is autonomously active, this would interfere with the detection of an autonomously active receptor. Since a new BCR is cloned into the cell, a pre-BCR is undesirable because it would appear on the surface with the desired heavy chain (HC) in combination with the undesired surrogate light chain and would disturb the selection.

the knockout of SLP65, an adapter protein of central importance in the BCR signaling pathway, prevents the activation of the TKO cell by a possibly reconstructed BCR.

The combination of the knockouts of RAG2 or RAG1 and Lambda5 leads to a blockade in the transition from the pro-B cell stage to the pre-B cell stage, which is classically characterized by the beginning rearrangement of the VDJ segments of the heavy chain (HC). Therefore they are pro-/pre-B cells.

Knockout of RAG2 or RAG1 and Lambda5 is sufficient for expression of the BCR and selection of the appropriate antibody. The activity of the BCR can be measured by reconstitution with the inducible SLP65.

The method of choice here is the measurement of Ca-flux after induction of SLP65 using FACS analysis and the use of a $Ca^{2+}$ dependent dye such as Indo-1. These methods are known to the expert (see M. Dühren-von Minden et. al; Nature 2012).

The first two knockouts ensured that only the "BCR of Interest" was expressed on the surface. By using an inducible SLP-65 to reconstitute the cells, the function of the expressed BCRs can be characterized and the autonomously active state of the BCRs on the surface can thus be verified before selection.

With these cells as "targets", FACS has now been used to identify an antibody that specifically binds to the modified region that induces and characterizes the autonomous activation of BCR. And this, although a binding to the same receptor type in RAMOS cells was not successful!

The cells carrying the "BCR of Interest" on the surface were first incubated with the pooled supernatants, and after a few washing steps the bound antibodies were detected using secondary antibodies. For a specific selection TKO cells (TKOs) were used, which expressed different versions of the "BCR of Interest". The selection matrix shown in FIG. 1 is exemplary for the selection of a CLL subset 2 BCR and was used for the identification and selection of positive clones. For easier identification, the supernatants of the hybridomas were pooled and measured. The groups that showed a binding were isolated and the supernatants of the respective hybridomas were tested for binding.

Confirmation that the selected antibody binds specifically to the modified BCR and not to other BCR variants was obtained using two blank samples, i.e. cells without BCR (see FIG. 1 A) and cells with non-CLL-BCR (see FIG. 1 E). Primary B-cells from the blood of leukemia patients were tested for binding using FACS. The selected antibody was able to specifically identify those BCRs that exhibited the target structure. This was confirmed at genomic level. Samples without this target structure showed no binding.

The invention is explained in more detail below using examples, taking FIG. 1 into account.

EXAMPLE 1

The starting point for the production of triple knockout cells (TKO) is formed by transgenic mice which have a respective knockout for the genes Lambda5, RAG2 and SLP-65 (Dühren von Minden et al., 2012, Nature 489, p. 309-313). The production of such mice is known to the expert and belongs to the state of the art. To obtain the cells, the bone marrow of the femur was extracted from the mice after they had been sacrificed. The cells obtained in this way were then cultured under conditions that promote the survival of pro-/pre-B cells (37° C., 7.5% $CO_2$, Iscoves medium, 10% FCS, P/S, murine IL7). After several passages, FACS sorting was carried out for control purposes, the pro-/pre-B cells were sorted and then returned to culture. The markers used for this purpose are known to the specialist.

For reconstitution with a 'BCR of interest', the corresponding sequences coding for the heavy (HC) and light (LC) chains were synthesized and then cloned into respective expression vectors each having a CMV promoter. These were introduced into the packaging cell line (Phoenix cell line) by lipofection. After 36 hours of incubation, the virus supernatant was removed and used for Spinfektion of the TKO cells. Both the work to extract the supernatants and the Spinfektion of the TKO are widely known procedures and known to experts.

The structural characteristics of subset-2 B-cell receptors were taken from the corresponding literature (see above). Exemplary CLL subset 2 VH and complete LC DNA segments were synthesized by a contract manufacturer using a standard procedure. These were then fused with a murine IgG1 constant segment by PCR and cloned into a CMV vector. The sequence of the finished vector was confirmed by Sanger sequencing.

```
CLL subset 2 VH (SEQ ID NO. 5):
EVQLVESGGGGGLGLVKPGGSLRLSCAASGFTFRSYSMNWVRQAPGKGLEW

VSSIISSSSYIYADSVKGRFTISRDNAKNSLYLQMNSLRAEDTALYYCARD

QNAMDVWGGTTVTVSS

CLL subset 2 LC (SEQ ID NO. 6):
SYELTQPPSVSVSVAPGKTARITCAGNNIGSKSVHWYQQQQAPVLVIYY

DSDRPSGIPERFSGSNSGNTATLTISRVEAGDEADYYCQVWDSGSDHPWWV

FGGGTKLTVLRQPKAAPSVTLFPPSSEELQANKATLVCLISDFYPGAVTVA

WKADSSPVKAGVETTTPSKQSNNKYAASSYLSLTPEQWKSHRSYSCQVTHE

GSTVEKTVAPTECS
```

A human cellular expression system based on HEK293T cells was used for the expression of the CLL subset 2 IgG1. A polyethyleneimine (PEI) based protocol was used for transfection. After several passages, the supernatant was pooled and the medium contained in the combined cell supernatant was purified using Protein G columns. The purity and quality of the soluble subset-2 IgG1 was determined by Western blotting.

Monoclonal antibodies were produced using the standard procedure in mice and the subsequent generation of hybridoma cells. The screening for positive clones was not performed by ELISA as usual. Since the target structure is a membrane-bound receptor, it is of central importance to validate the binding of the potential antibodies in a cellular system, i.e. while largely preserving the cell physiological states native to this cell type. First, groups of pooled supernatants were examined for binding events using FACS analysis. For this purpose different CLL-Subset 2 BCR variants were expressed on the surface of a cell line (TKO), which cannot express BCR itself. The first step was to identify the supernatants whose antibodies showed a binding. Subsequently, the supernatants of the individual hybridoma clones were examined in more detail with regard to their binding in order to identify highly specific clones with a high affinity.

For the screening procedure, different vectors were used in the previous transformation for the following heavy chain (HC) and light chain (LC) combinations of the corresponding CLL-BCRs, these combinations being used on the surface of the BCR reconstitution system:

Control (transformation vector without BCR) (see FIG. 1 A)

Vector with HC/LC typical for the CLL subset 2 (see FIG. 1 B)

Vector with a non-CLL subset 2 HC/a LC typical for the CLL subset 2 (without target motif; epitope) (see FIG. 1 C)

Vector with HC typical for the CLL subset 2/a non-CLL subset 2 LC (see FIG. 1 D)

Vector with one non-CLL subset 2 HC/one non-CLL subset 2 LC (see FIG. 1 E)

Vector with HC/LC typical for the CLL subset 2 (including mutation R110G (target motif)) (see FIG. 1 F).

This selection procedure is illustrated schematically in FIG. 1 using the example of the CLL subset 2 BCRs, where the term 'TKO' refers to TKO cells (see above).

In the 1st selection round, supernatants of several clones were combined and examined with regard to their binding profile to the selection matrix. A positive binding profile is given if a specific binding to the "BCR-of-Interest" is shown. Groups showing such a profile were isolated, and the binding profile of the individual clones was characterized again on the selection matrix during a second selection round. The binding of the monoclonal antibodies was verified using a FACS binding assay using a fluorescence-labeled Anti-Mouse-IgG antibody. Call it: A) no BCR (control); B) a CLL-Subset2 typical BCR; C) a BCR with random heavy chain and a CLL-Subset2 typical light chain; D) a BCR with a CLL-Subset2 typical heavy chain and a random light chain; E) a BCR with arbitrary heavy and light chain (control; not CLL-Subset2 typical BCR); F) a CLL-Subset2 typical BCR with a mutation in the target motive (R110G) (control).

Based on the finding that the antibody only binds to the cells with the target structures (CLL-Subset2 BCR; FIG. 1B), it can be concluded that an antibody is present that specifically binds to cells with autonomously active receptors.

It was shown that the use of cells in the pro-/pre-stage of B cell development is necessary for the exact expression of the BCR required for detection. These cells are genetically capable of representing new BCR by exact folding and expression on their surface. The inactivation (knockout) of RAG2 and Lambda5 prevents the expression of an endogenous BCR or pre-BCR. The deletion of SLP65 and the subsequent reconstruction of an inducible SLP65 makes it possible to characterize the activity level of the "BCR of interest".

To determine the amino acid sequence of the monoclonal antibodies selected by selection, mRNA was isolated from the individual hybridoma clones, cDNA was generated from them and amplified by Anchor PCR (Rapid expression cloning of human immunoglobulin Fab fragments for the analysis of antigen specificity of B cell lymphomas and anti-idiotype lymphoma vaccination; Osterroth F, Alkan O, Mackensen A, Lindemann A, Fisch P, Skerra A, Veelken H., J Immunol Methods 1999 Oct. 29; 229 (1-2):141-53).

For the generation of the monoclonal antibodies, synthetic peptides which represented the regions for the ability of an autonomous signal were used in addition to the complete immunoglobulins.

The specific monoclonal antibody against Subset-2 was sequenced. The following amino acid sequences were determined: SEQ ID NO. 9 for the variable part of the heavy chain (HC), SEQ ID NO. 10 for the variable part of the light chain (LC), and CDR 1, 2 and 3 (marked in bold) in the order given.

```
(AVA-mAb01 HC)
                                          SEQ ID NO. 9
QVQLQQQQSGPGLGLVQPSQSLSITCTVSGFSLTSYGIHWRQSPGKGLEWL

GVIWRGGGTDSNAAFMSRLSITKDNSKSQVFFKMNSLQADDTAIYYCARSR

YDEEESMNYWGQGTSVIVSS (AVA-mAb01 LC)
                                         SEQ ID NO. 10
QIVLTQSPASLSASVGETVTITCRASGNIHSYLAWYQQKQGKSPQLLVYNA

KTLADGVPSRFSGSGSGTQYSLKINSLQPEDFGSYYCQHFWNTPPTFGAGT

KLELK
```

The partial sequences of the heavy chain corresponding to CDR1, CDR2 and CDR3 according to SEQ ID NO. 9 are included in SEQ ID NOS. 11 to 13, while the partial sequences of the light chain corresponding to CDR1, CDR2 and CDR3 according to SEQ ID NO. 10 in SEQ ID NOS. 14 to 16 are shown.

```
(AVA-mAB01 CDR1 HC)
                                         SEQ ID NO. 11
GFSLTSYG (AVA mAB01 CDR2 HC)
                                         SEQ ID NO. 12
IWRGGGT (AVA mAB01 CDR3 HC)
                                         SEQ ID NO. 13
ARSRYDEEESMNY (AVA mAB01 CDR1 LC)
                                         SEQ ID NO. 14
GNIHSY (AVA mAB01 CDR2 LC)
                                         SEQ ID NO. 15
NAKT (AVA mAB01 CDR3 LC)
                                         SEQ ID NO. 16
QHFWNTPPT
```

The procedure described above is exemplary for the generation of antibodies specific to CLL-Subset 2. The same process was also performed using specific sequences and isotypes for subset 4.

Exemplary CLL subset 4 VH and complete LC DNA segments were synthesized by a contract manufacturer using a standard procedure. These were then fused with a murine IgG1 constant segment by PCR and cloned into a CMV vector. The sequence of the finished vector was confirmed by Sanger sequencing.

```
CLL subset 4 HC (SEQ ID NO. 7):
QVQLQQWGAGLLKPSETLSLTCAVYGGSFSGYYWTWIRQSPGKGLEWIGEI

NHSGSTTYNPSLKSRVTISVDTSKNQFSLKLNSVTAADTAVYYCARGYGDT

PTIRRYYYGMDVWGQGTTVTVSSASTKGPSVFPLAPSSKSTSGGTAALGC

LVKDYFPEPVTVSWNSGALTSGVHTFPACLQSSGLYSLSSVVTVPSSSLGT

QTYICNVNHKPSNTKVDKKC
```

The bold regions indicate the target sequences (epitopes) of the variable part of the heavy chain of the BCR of subset 4 responsible for its autonomously active state (see SEQ ID NOS. 3 and 4).

```
CLL subset 4 LC (SEQ ID NO. 8):
DIVMTQSPLSLPVTLGQPASISCRSSQSLVHSDGNTYLNWFQQRPGQSPRR

LIYKVSDRDSGVPDRFSGSGSGTDFTLKISRVEAEDVGLYYCMQGTHWPPY

TFGQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVTH

QGLSSPVTKSFNRGEC.
```

EXAMPLE 2

A small amount of peripheral blood was taken from a patient using the invention. For the analysis 100 µl blood were transferred into a reaction vessel and filled with 2 ml PBS-BSA buffer solution. The sample was then centrifuged in an Eppendorf 5804 centrifuge at 1500 rpm for a period of five minutes. The supernatant was discarded and the sediment was well mixed. The antibody was then added. Staining was performed against the following surface parameters: 1) CD19-FITC, 2) CD5-PE, and 3) CLL SubSet-2 specific antibody (APC), before incubation at room temperature in the dark for 15 minutes. Lysis was then initiated and the erythrocytes were lysed. As described above, the cells were washed twice with PBS-BSA buffer solution and were resuspended in 500 µl 0.1% PBS-BSA buffer solution. The cells were kept in the dark at 2-8° C. until measurement on the flow cytometer.

Figure 2:
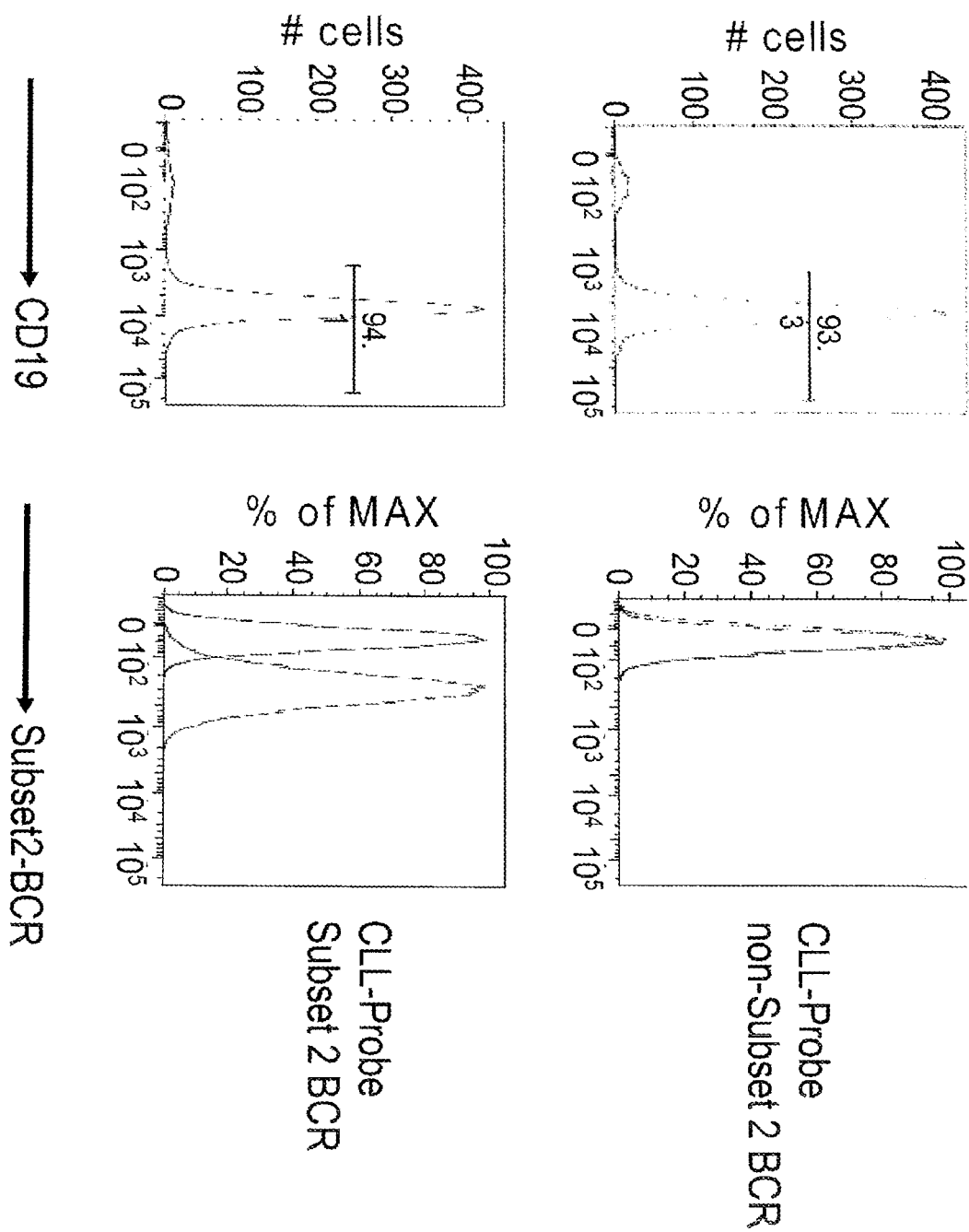
FIG. 2 illustrates an example of FACS analysis performed on peripheral blood from a patient suffering CLL using Subset-2 specific antibody. In a first step, CD19 positive B cells were selected for further analysis (left panel). These were then examined for the binding of the specific antibody (right panel), either CLL-Probe Subset 2 BCR or CLL-Probe non-Subset 2 BCR.

The analysis at the FACS was performed on a BDCalibur. The setting of the individual laser and detection parameters was carried out according to the instructions of the device manufacturer and is sufficiently known to the specialist. The raw data of the analysis were then evaluated using FlowJo analysis software. First, the lymphocyte population was selected and marked in the FSC/SSC blot. For this selection it was then focused on the CD19-positive B-cells and the binding of the Subset-2 specific antibody was analyzed. FIG. 2 shows an example of such an analysis using the example of the use of the Subset-2 specific antibody. In a first step, the CD19 positive B cells were selected for further analysis (left panel). These were then examined for the binding of the specific antibody (right panel).

The invention claimed is:

1. A diagnostic method for detecting autonomously active or autonomously activated B-cell receptors in a sample comprising adding to the sample an isolated antibody or functional fragment thereof, wherein a partial sequence of the heavy chain of the isolated antibody or functional fragment thereof corresponding to CDR1 is SEQ ID NO: 11, corresponding to CDR2 is SEQ ID NO: 12, and corresponding to CDR3 is SEQ ID NO: 13, and a partial sequence of the light chain of the isolated antibody or functional fragment thereof corresponding to CDR1 is SEQ ID NO: 14, corresponding to CDR2 is SEQ ID NO: 15, and corresponding to CDR3 is SEQ ID NO: 16, wherein said isolated antibody or functional fragment thereof selectively binds to autonomously active or autonomously activated B-cell receptors, and wherein the autonomously active or autonomously activated B-cell receptors are characterized by the presence of structural domains or epitopes to which the isolated antibody or functional fragment thereof selectively binds and which are causative for the autonomously active or autonomously activated state of the B-cell receptors.

2. The diagnostic method according to claim 1, characterized in that the isolated antibody or functional fragment thereof selectively binds to target sequences of the B cell receptor which are characteristic for subset 2.

3. The diagnostic method according to claim 2, characterized in that the isolated antibody or functional fragment thereof binds to a region of the B cell receptor characterized by the presence of an amino acid sequence selected from the group consisting of

```
(i)
                                            (SEQ ID NO: 1)
KLTVLRQPKA,
and
```

```
(ii)
                                            (SEQ ID NO: 2)
VAPGKTAR.
```

4. The diagnostic method according to claim 1, characterized in that the isolated antibody or functional fragment thereof comprises at least one fluorescent dye.

5. The diagnostic method according to claim 1, characterized in that the isolated antibody or functional fragment thereof does not bind to receptors or other membrane structures of B cells which do not have a structural domain or epitope which are causative for the autonomously active or autonomously activated state of the B cell receptors.

6. The diagnostic method according to claim 5, characterized in that the isolated antibody or functional fragment thereof does not bind to target sequences of the B cell receptor which are not characteristic for subset 2.

7. The diagnostic method according to claim 6, characterized in that the isolated antibody or functional fragment thereof does not bind to a B cell receptor which does not have any of the sequences selected from the group consisting of

```
(i)
                                            (SEQ ID NO: 1)
KLTVLRQPKA,
and
```

```
(ii)
                                            (SEQ ID NO: 2)
VAPGKTAR.
```

8. The diagnostic method according to claim 1, wherein said detecting autonomously active or autonomously activated B-cell receptors provides for the diagnosis of malignant B-cell neoplasia.

* * * * *